United States Patent [19]

Paxson

[11] Patent Number: 4,717,785

[45] Date of Patent: Jan. 5, 1988

[54] REMOVAL OF PHOSPHINE IMPURITIES FROM HIGHER OLEFINS

[75] Inventor: Timm E. Paxson, Houston, Tex.

[73] Assignee: Shell Oil Company, Houston, Tex.

[21] Appl. No.: 940,386

[22] Filed: Dec. 10, 1986

[51] Int. Cl.$^4$ .............................. C07C 7/12; C07C 2/02
[52] U.S. Cl. ..................................... 585/823; 585/523; 585/527
[58] Field of Search ............... 585/864, 865, 830, 514, 585/523, 527, 823

[56] References Cited

U.S. PATENT DOCUMENTS

| | | | |
|---|---|---|---|
| 3,247,242 | 4/1966 | McGarvey et al. | 585/823 X |
| 3,409,691 | 11/1968 | Small | 585/830 |
| 3,424,810 | 1/1969 | Suatoni | 585/830 |
| 3,574,139 | 4/1971 | Harder | 585/827 X |
| 4,472,525 | 9/1984 | Singleton | 585/527 X |
| 4,503,279 | 3/1985 | Singleton | 585/527 X |
| 4,518,814 | 5/1985 | Knudsen et al. | 585/523 |
| 4,528,415 | 7/1985 | Knudsen | 585/527 |

FOREIGN PATENT DOCUMENTS 7605824  6/1975  Netherlands ......................... 585/823

*Primary Examiner*—Andrew Metz
*Assistant Examiner*—Glenn Caldarola

[57] ABSTRACT

Phosphine impurities are effectively removed from higher olefin products containing such impurities by treatment of the olefin with a macroreticular cation exchange resin in the acid form. The invention is particularly useful in removing phosphine catalyst residues from the $C_6$ and higher mono-olefin products of ethylene oligomerization reactions.

20 Claims, No Drawings

REMOVAL OF PHOSPHINE IMPURITIES FROM HIGHER OLEFINS

BACKGROUND OF THE INVENTION

This invention relates to a process for the purification of higher olefins by removal therefrom of phosphine impurities, particularly phosphine impurities representing residues of catalysts utilized in preparation of the olefins.

It is known in the art to prepare higher olefins (i.e., those having a carbon number of at least six) by the oligomerization of lower olefins, most commonly ethylene, over a catalyst which comprises a phosphine component. Such oligomerization processes are described, for instance, in U.S. Pat. No. 4,528,416 and other patents cited therein.

Higher olefins find their principal utility as intermediates in the preparation of a very wide variety of end products. For example, olefin products having carbon numbers predominantly in the $C_6$ to $C_{20}$ range are known to be particularly useful as intermediates in the preparation of surfactants, lubricants, polymers and plasticizers. In the practice of various processes for synthesizing such end products from higher olefins, it has on occasion been observed that small amounts of residual phosphine impurities substantially interfere with the processing of the olefin or adversely influence the properties of the end product. Accordingly, a process for the effective removal of phosphine impurities from higher olefins would be highly desirable.

The present invention most particularly relates to a process for the removal of phosphine impurities from an olefin containing such impurities, which comprises a step for the contact of the olefin with a cation exchange resin in the acid, or hydrogen ion, form. In this respect, the prior art is found to disclose that an anion exchange resin can be used to eliminate phosphate values from water. U.S. Pat. No. 3,579,322 specifically describes contacting a waste aqueous stream containing phosphate values with a cation exchange resin bed to remove cations followed by contact of the cation-free stream with an anion exchange resin to eliminate the phosphate values. In an alternative process, this patent teaches contact of the aqueous stream directly with a weak-base anion exchange resin for removal of phosphate values. The published Japanese patent application No. 5 5-8017-885 describes contact of water containing both phosphate and a magnesium salt with an ion exchange resin in the calcium form. This contact yields an ion exchange in the magnesium form, and calcium phosphate which can be precipitated from aqueous solution. The published Japanese application No. 5-3031-572 discloses a process for removal of phosphoric acid ions from aqueous solution using an ion exchange means exemplified by $Al_2O_3$, $La_2O_3$, and Group VIII metal oxides.

SUMMARY OF THE INVENTION

It has now been found that phosphine impurities can be effectively removed from higher olefin products containing such impurities by treatment of the olefin with a particularly specified cation exchange resin. The resin is necessarily a macroreticular resin in the acid form. Strong acid resins and particularly sulfonated resins are preferred.

Accordingly, the present invention can be briefly described as a process for removing phosphine impurities from a higher olefin product, which comprises contacting the said higher olefin product with a macroreticular cation exchange resin in the acid form.

DESCRIPTION OF THE PREFERRED EMBODIMENTS

Although it is more broadly applicable to the treatment of any phosphine-containing higher olefin, the invention is particularly useful in applications for the removal of phosphine impurities from the higher olefin products of oligomerization processes utilizing phosphine-containing catalyst systems. Various processes for the oligomerization of lower olefins to higher olefin products, utilizing as catalysts a class of chelate complexes of metals, particularly nickel, with organophosphines, are described in U.S. Pat. No. 4,528,416 to Lutz, U.S. Pat. No. 4,260,844 to O'Donnell et al, U.S. Pat. No. 4,020,121 to Kister et al, U.S. Pat. No. 3,825,615 to Lutz, U.S. Pat. No. 3,647,915 to Bauer et al, U.S. Pat. No. 3,647,914 to Glockner et al, U.S. Pat. No. 3,644,564 to Van Zwet et al, and U.S. Pat. No. 3,737,475, U.S. Pat. No. 3,686,351, and U.S. Pat. No. 3,676,523 all to Mason. The disclosures of these patents are incorporated herein by this reference, insofar as they pertain to processes which provide opportunity for the introduction of phosphine compounds into higher olefins products. Oligomerization, as the term is used herein, is intended to include dimerization reactions, trimerization reactions, and the higher oligomerization reactions by which ethylene, propylene, and butylene starting materials are converted to higher olefinic oligomers.

In conventional practice, when higher olefins are prepared via oligomerization of lower olefins (for instance $C_2$ to $C_4$ olefins and particularly ethylene) in the presence of a catalyst system comprising a phosphine component, it is typical for the finished olefin product to contain phosphine impurities, particularly organophosphine impurities, in quantities corresponding to a concentration of elemental phosphorus on the order of 10 to 100 ppmw (parts per million, by weight). The phosphine impurities found in a given higher olefin product of such an oligomerization process may represent the particular phosphine compound used in forming the oligomerization catalyst system (for instance, a diarylphosphinocarboxylic acid) or, alternatively, may be in the form of one or more other phosphine compounds (for instance, a diarylalkyl phosphine) to which that particular phosphine is converted during the oligomerization reaction or the finishing of the olefin product.

Preferably, the invention is applied to remove phosphine impurities which are predominantly organophosphine compounds from olefins which are predominantly acyclic aliphatic olefins and have carbon numbers which are predominantly in the range from about 6 to about 30. The invention is particularly useful for removing phosphine impurities from mono-olefins having carbon numbers predominantly in the range from about 6 to 20.

The cation exchange resin used in the process of the invention is necessarily a macroreticular (macroporous, highly crosslinked) resin in the acid form, that is, a resin having a negatively charged matrix and exchangeable hydrogen cations. The resin in suitably of the weak acid type, as exemplified by common conventional resins based on acrylic or methacrylic acid that has been cross-linked with a difunctional monomer such as divinylbenzene. Strong acid resins are, however, preferred. Of particular interest for use in the invention are the strong acid resins which are sulfonated resins wherein the exchangeable hydrogen cation is provided by the $SO_3H$ moiety. Such sulfonated, strong acid resins are exemplified by the sulfonated copolymers of styrene and divinylbenzene.

Specific examples of commercially available macroreticular sulfonated strong acid ion exchange resins include those described in the following table:

| Resin | Manufacturer | Surface Area ($m^2$/g) | Average Pore Diameter (A) |
|---|---|---|---|
| Amberlyst 15 | Rohm & Haas Co. | 45–55 | 265 |
| Amberlite 200 | Rohm & Haas Co. | 35–45 | |
| XN-1010 | Rohm & Haas Co. | 570 | 50 |
| XN-1005 | Rohm & Haas Co. | 130 | 175–210 |
| MSC-1-H | Dow Chemical Co. | 35 | 300 |
| AG-MP-50 | Bio-Rad Lab., Inc. | 30–50 | |
| Duolite C26TR | Diamond Shamrock Corp. | 15–30 | |

For purposes of the invention, the liquid olefin containing one or more phosphine impurities is contacted with the solid resin, suitably in either a batch or continuous (or semi-continuous) mode. When operating in a batch mode, the contact preferably involves agitation of a mixture of the olefin and the resin for about 0.01 to 10 hours, more preferably 0.1 to 3 hours, followed by separation of the resin by conventional solid-liquid separation techniques, e.g., settling, centrifugation, filtration, or the like. The invention is often more conveniently practiced in a continuous mode by passing a stream of the olefin through one or more contained beds of the resin, e.g., fixed beds, moving beds, or fluidized beds, at a flowrate preferably ranging from a weight hourly space velocity of about 0.1 to 100 hours−1, and more preferably from about 0.5 to 10 hours−1. The invention is very suitably practiced in conventional contactors designed for ion exchange service.

The conditions of the contact treatment of the higher olefin with the cation exchange resin are not narrowly critical to the performance of the invention. Nevertheless, preference can be expressed for certain specified operating ranges. For instance it is preferred that contact of the olefin with the cation exchange resin take place at a temperature in the range from about 5° to 100° C., more preferably in the range from about 5° to 70° C. and most preferably in the range from about 10 to 55° C. More broadly, operating temperatures are only limited by the freezing point and boiling point of the olefin and the temperature stability of the resin. Process pressure is specified only in terms of a pressure sufficient to maintain the olefin in the liquid phase. Atmospheric or greater pressures (e.g., 1–100 bar) and typical ambient temperatures (i.e., 10°–35° C.) are preferred for convenience.

After the contact step, the resin may, if desired, be regenerated for reuse, although regeneration is not a necessary aspect of the invention. In cases in which the phosphine impurities are initially present in the feedstock in a low concentration (e.g., up to 50 ppmw), the invention can in many cases be economically practiced with a "throw-away bed", without regeneration of the resin. In this regard, it has been found that for treatment of the olefin products of most interest, a bed can typically be used to treat a quantity of olefin up to about 500 times its own weight before there is a significant loss in its phosphine removal capabilities. Capacity of the resin bed for treatment of olefin will, of course, in any given case be dependent upon the particular concentration of phosphine impurities in the olefin feedstock. If regeneration of the resin bed is desired, it can be accomplished by conventional methods, involving, for instance, treatment of the resin with an acid wash (e.g., aqueous or alcoholic hydrochloric acid or acetic acid, or the like), followed by water wash to restore the hydrogen cations in the resin. Following such treatment, the resin is preferably dried to remove excess water before reuse.

Practice under the invention at preferred operating conditions has been found to be capable of reducing the phosphine content of the olefin to a level of less than 1 part per million.

The invention is further described with reference to the following example, which is intended to illustrate a certain preferred embodiment and not to limit its broader scope. Comparative experiments are also provided, showing the relatively poor phosphine removal performance of practices not in accordance with the invention, using common ion exchange materials other than the specified acid ion exchange resin.

EXAMPLE

In an experiment in accordance with practice under this invention, a stream of $C_{16}$ alpha-olefins having predominantly linear carbon structure was contacted with a bed of a macroreticular cation exchange resin in the acid form. The alpha-olefin stream had been prepared by oligomerization of ethylene using a phosphine-containing catalyst, and had a residual content of phosphine (primarily ethyldiphenyl phosphine) determined by chromatography to represent about 30–35 ppmw of elemental phosphorus. The bed consisted of two sections of resin, through which the olefin flowed in series, and had provision for withdrawal of a sample of the olefin between the two sections. Use of the divided, two-section, bed and a flow of olefin in series through the two sections permitted investigation at two space velocities in each experiment. In each case the bed was operated in an upflow mode and at a temperature of about 80° F.

The $C_{16}$ olefin stream was contacted with a bed of Dowex MSC-1-H+ cation exchange resin. The MSC-1-H+ resin is a strongly acidic sulfonated macroreticular resin characterized by a surface area of about 35 square meters per gram, an average pore diameter of 300A, and an acid density of 4.0 milliequivalents acid (H+) per gram. Prior to use, the material was washed with 5 bedweights of 0.1 normal hydrochloric acid solution, then with 10 bedweights of water. Finally, the resin was dried at 100° C. in a flowing nitrogen atmosphere. Flowrate of the olefin was set to provide a weight hourly space velocity (WHSV) of 5.0 in the first of the two bed sections and a WHSV of 2.5 in the overall bed. Results are shown in Table 1, in terms of the amount (in parts per million by weight) of phosphorus in the effluent olefin, were determined over the duration (in hours) of the experiment, and for the number of bedweights of olefin which had been contacted with the resin (i.e., the ratio of the cumulative weight of the olefin stream to the weight of the resin with which it was contacted).

TABLE I

| | WHSV 5 | | WHSV 2.5 | |
|---|---|---|---|---|
| Hours | Throughput (Bedweights) | Elemental Phosphorus (ppmw in effluent) | Throughput (Bedweights) | Elemental Phosphorus (ppmw in effluent) |
| 0 | 0.0 | | 0.0 | |
| 8 | 27.3 | 21.0 | 13.1 | 0.5 |
| 16 | 74.5 | 0.9 | 36.7 | 0.0 |
| 24 | 126.4 | 4.3 | 10.3 | 0.0 |
| 32 | 161.2 | 5.1 | 80.0 | 0.1 |
| 40 | 189.1 | 3.9 | 93.9 | 0.1 |
| 48 | 236.9 | 13.5 | 117.9 | 0.3 |
| 56 | 266.9 | 18.3 | 132.9 | 0.4 |
| 64 | 302.1 | 6.1 | 150.5 | 0.3 |
| 72 | 343.2 | 25.7 | 171.0 | 0.7 |
| 80 | 366.3 | 27.3 | 182.5 | 1.6 |
| 88 | 401.1 | 19.9 | 199.9 | 2.3 |
| 96 | 441.9 | 26.8 | 220.3 | 2.7 |
| 104 | 473.1 | 30.4 | 235.9 | 6.5 |

These results indicate a very effective removal of the phosphine impurities up to cumulative olefin contact flows of about 200 bedweights, which roughly corresponds to adsorption of a basic phosphorus atom of the phosphine at each available acid ($SO_3H$) site of this resin.

COMPARATIVE EXPERIMENT A

This comparative experiment illustrates a practice not according to the invention in which the $C_{16}$ olefin is contacted with a bed of alumina. Apart from this substitution of ion exchange material, this experiment was conducted under the same procedures used in the above Example 1. The specific alumina tested was KC-300 alumina, a product of Shell Chemical Company, characterized by a surface area of about 200–400 square meters per gram. The material was in the form of a one-tenth inch diameter cylindrical extrudate. The resin was dried at 525° C. for 10 hours in a flowing nitrogen stream before use.

Results for this comparative experiment are presented in Table II:

TABLE II

| | WHSV 5 | | WHSV 2.5 | |
|---|---|---|---|---|
| Hours | Throughput (Bedweights) | Elemental Phosphorus (ppmw in effluent) | Throughput (Bedweights) | Elemental Phosphorus (ppmw in effluent) |
| 0 | 0.0 | | 0.0 | |
| 4 | 9.8 | 2.7 | 4.9 | 0.4 |
| 8 | 29.0 | 8.5 | 14.5 | 0.6 |
| 12 | 45.5 | 11.8 | 22.8 | 2.6 |
| 16 | 61.5 | 12.5 | 30.8 | 3.0 |
| 20 | 78.0 | 16.0 | 39.0 | 2.6 |
| 24 | 96.5 | 18.6 | 48.3 | 6.1 |
| 28 | 110.0 | 15.9 | 55.0 | 4.8 |
| 32 | 127.0 | 24.9 | 63.5 | 10.6 |
| 36 | 143.0 | 23.3 | 71.5 | 4.3 |
| 40 | 161.3 | 13.2 | 80.6 | 6.5 |
| 44 | 180.3 | 12.2 | 90.1 | 5.8 |
| 48 | 198.8 | 13.6 | 99.4 | 7.3 |
| 52 | 215.0 | 26.6 | 107.5 | 14.7 |
| 56 | 233.3 | 27.0 | 116.6 | 16.4 |
| 60 | 247.3 | 22.7 | 123.6 | 12.4 |
| 64 | 261.8 | 14.0 | 130.9 | 17.5 |
| 68 | 277.8 | 28.0 | 138.9 | 19.4 |
| 72 | 291.8 | 34.2 | 145.9 | 21.1 |
| 76 | 309.3 | 20.3 | 154.6 | 17.2 |
| 80 | 331.3 | 26.9 | 165.6 | 21.0 |
| 84 | 349.8 | 23.8 | 174.9 | 0.0 |
| 88 | 365.5 | 31.3 | 182.8 | 27.2 |

These results show that, compared to practice according to the invention, alumina is substantially less effective for the removal of phosphines from higher olefins. Although the alumina did not offer acceptable performance for removal of phosphine impurities, it was found to be effective for removal of certain oxygenated impurities from the olefin. In a preferred embodiment, the invention is practiced with a contact of the olefin with both the specified acid resin and alumina, either in multiple beds or a single mixed bed to achieve removal of both phosphines and other impurites.

COMPARATIVE EXPERIMENT B

For this comparative experiment, again not in accord with the present invention, the $C_{16}$ olefin was contacted with a bed of 13-X zeolite, a product of the Linde Division of Union Carbide Corporation. The material was in the form of a one-sixteenth inch diameter cylindrical extrudate. Before use, the resin was dried at 250° C. for four hours in a flowing nitrogen stream. Apart from this substitution of ion exchange material, this experiment was conducted under the same procedures used in the above Example 1.

Results for this comparative experiment are presented in Table III:

TABLE III

| | WHSV 5 | | WHSV 2.5 | |
|---|---|---|---|---|
| Hours | Throughput (Bedweights) | Elemental Phosphorus (ppmw in effluent) | Throughput (Bedweights) | Elemental Phosphorus (ppmw in effluent) |
| 0 | 0.0 | | 0.0 | |
| 4 | 14.8 | 4.4 | 7.4 | 0.0 |
| 8 | 30.8 | 15.6 | 15.4 | 1.5 |
| 12 | 50.4 | 17.8 | 25.2 | 3.4 |
| 16 | 68.8 | 20.7 | 34.4 | 7.0 |
| 20 | 87.4 | 19.4 | 43.7 | 8.7 |
| 24 | 105.0 | 20.8 | 52.5 | 10.8 |
| 28 | 119.4 | 21.5 | 59.7 | 10.8 |
| 32 | 138.2 | 21.5 | 69.1 | 10.9 |
| 36 | 154.8 | 22.9 | 77.4 | 13.0 |
| 40 | 173.4 | 23.9 | 86.7 | 12.2 |
| 44 | 191.2 | 21.5 | 95.6 | 12.6 |
| 48 | 207.8 | 21.3 | 103.9 | 13.5 |
| 52 | 222.8 | 12.4 | 111.4 | 12.4 |
| 56 | 238.4 | 13.2 | 119.2 | 13.2 |
| 60 | 253.4 | 12.4 | 126.7 | 12.4 |
| 64 | 272.0 | 13.9 | 136.0 | 13.9 |
| 68 | 288.2 | 20.2 | 144.1 | 14.0 |
| 72 | 295.8 | 27.4 | 147.9 | 20.2 |
| 76 | 309.8 | 27.2 | 154.9 | 16.5 |
| 80 | 329.2 | 25.6 | 164.6 | 19.0 |
| 84 | 346.8 | 16.3 | 173.4 | 21.7 |
| 88 | 355.1 | 31.1 | 177.6 | 22.9 |

These results again illustrate the criticality for use in the invention of the specified acid ion exchange resin for effective removal of the phosphines impurities.

COMPARATIVE EXPERIMENT C

For this comparative example, again not in accord with the present invention, the $C_{16}$ olefin was contacted with a bed of activated carbon, specifically a 60/80 mesh granular activated carbon manufactured by the Calgon Corp. This material was water washed and dried at 250° C. prior to use. Apart from this substitution of ion exchange material, this comparative experiment was conducted under the same procedures used in the above Example 1.

Results for this comparative experiment are presented in Table IV:

TABLE IV

| | WHSV 5 | | WHSV 2.5 | |
|---|---|---|---|---|
| Hours | Throughput (Bedweights) | Elemental Phosphorus (ppmw in effluent) | Throughput (Bedweights) | Elemental Phosphorus (ppmw in effluent) |
| 0 | 0.0 | | 0.0 | |
| 8 | 30.3 | 0.0 | 14.5 | 4.9 |
| 16 | 80.3 | 27.3 | 39.5 | 25.2 |
| 24 | 128.5 | 32.8 | 63.7 | 26.8 |
| 32 | 161.2 | 4.0 | 80.0 | 37.0 |
| 40 | 196.5 | 38.7 | 91.6 | 16.7 |
| 48 | 242.7 | 31.3 | 120.7 | 40.9 |
| 56 | 273.3 | 35.5 | 136.1 | 37.4 |
| 64 | 310.0 | 13.0 | 154.4 | 33.2 |
| 72 | 352.0 | 27.3 | 175.4 | 37.1 |
| 80 | 376.3 | 34.7 | 187.5 | 45.7 |
| 88 | 412.0 | 39.7 | 205.4 | 34.3 |
| 96 | 454.4 | 33.4 | 226.6 | 32.1 |
| 104 | 485.6 | 34.4 | 242.2 | 29.3 |

These results show that, compared to practice according to the invention, activated carbon is substantially less effective for the removal of phosphines from higher olefins.

I claim as my invention:

1. A process for removing phosphine impurities from a higher olefin product containing such phosphine impurities, which comprises contacting the said higher olefin product with a macroreticular cation exchange resin in the acid form.

2. The process of claim 1, wherein the cation exchange resin is a sulfonated cation exchange resin.

3. The process of claim 2, wherein the sulfonated resin is a sulfonated copolymer of styrene and divinylbenzene.

4. The process of claim 1, wherein the contact of the higher olefin product with the macroreticular cation exchange resin takes place at a temperature in the range from about 5° to 100° C.

5. The process of claim 1, wherein the olefin is contacted with the resin at a weight hourly space velocity ranging from about 0.1 to about 100 hr−1.

6. The process of claim 5, wherein the contact of the higher olefin product with the macroreticular cation exchange resin takes place at a temperature in the range from about 5° to 70° C.

7. The process of claim 6, wherein the weight hourly space velocity of the olefin is in the range from about 0.5 to about 10 hours−1.

8. The process of claim 6, wherein the cation exchange resin is a sulfonated cation exchange resin.

9. The process of claim 8, wherein the sulfonated resin is a sulfonated copolymer of styrene and divinylbenzene.

10. The process of claim 1, wherein the phosphine impurities are predominantly organophosphine impurities present in the higher olefin product in a concentration of about 10 to 100 parts per million by weight, based on elemental phosphorus.

11. The process of claim 10, wherein the higher olefin product predominantly comprises acyclic aliphatic mono-olefins in the carbon number range from about 6 to 30.

12. A process for preparing and purifying a higher olefin product which comprises steps for oligomerizing one or more lower olefin reactants in the presence of a catalyst system comprising a chelate complex of nickel with an organophosphine to produce a higher olefin product containing phosphine impurities and contacting the said higher olefin product with a macroreticular cation exchange resin in the acid form to remove said phosphine impurities.

13. The process of claim 12, wherein the cation exchange resin is a sulfonated cation exchange resin.

14. The process of claim 13, wherein the sulfonated resin is a sulfonated copolymer of styrene and divinylbenzene.

15. The process of claim 14, wherein the contact of the higher olefin product with the macroreticular cation exchange resin takes place at a temperature in the range from about 5° to 70° C.

16. The process of claim 15, wherein the olefin is contacted with the resin at a weight hourly space velocity ranging from about 0.1 to about 100 hr−1.

17. The process of claim 16, wherein the phosphine impurities are predominantly organophosphine impurities present in the higher olefin product in a concentration of about 10 to 100 parts per million by weight, based on elemental phosphorus.

18. The process of claim 17, wherein the higher olefin predominantly comprises acyclic aliphatic mono-olefins in the carbon number range from about 6 to 30.

19. The process of claim 14, wherein the phosphine impurities are predominantly organophosphine impurities present in the higher olefin product in a concentration of about 10 to 100 parts per million by weight, based on elemental phosphorus.

20. The process of claim 19, wherein the higher olefin predominantly comprises acyclic aliphatic mono-olefins in the carbon number range from about 6 to 30.

* * * * *